United States Patent
Mori et al.

(10) Patent No.: US 7,252,876 B2
(45) Date of Patent: *Aug. 7, 2007

(54) LAMINATED ZEOLITE COMPOSITE AND METHOD FOR PRODUCTION THEREOF

(75) Inventors: Nobuhiko Mori, Nagoya (JP); Toshihiro Tomita, Nagoya (JP); Hitoshi Sakai, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 191 days.

This patent is subject to a terminal disclaimer.

(21) Appl. No.: 10/797,833

(22) Filed: Mar. 10, 2004

(65) Prior Publication Data

US 2004/0229027 A1    Nov. 18, 2004

Related U.S. Application Data

(63) Continuation of application No. PCT/JP02/09317, filed on Sep. 12, 2002.

(30) Foreign Application Priority Data

Sep. 17, 2001    (JP) ............................ 2001-281675

(51) Int. Cl.
- *B01D 39/00* (2006.01)
- *B32B 3/00* (2006.01)
- *B01J 29/04* (2006.01)
- *B01J 29/06* (2006.01)

(52) U.S. Cl. ............... 428/312.2; 428/312.6; 428/212; 210/506; 210/210.1; 502/60; 502/63; 502/64; 502/71; 502/4

(58) Field of Classification Search ............... 428/212, 428/304.4, 446, 689, 312.2, 312.6, 702; 502/4, 502/60, 64, 71, 77, 63; 210/506, 510.1
See application file for complete search history.

(56) References Cited

U.S. PATENT DOCUMENTS

| | | | |
|---|---|---|---|
| 5,110,478 A | | 5/1992 | Haag et al. |
| 6,037,292 A | * | 3/2000 | Lai et al. ............ 502/60 |
| 6,090,289 A | | 7/2000 | Verduijn et al. |
| 6,936,560 B2 | * | 8/2005 | Mori et al. ............ 502/4 |

FOREIGN PATENT DOCUMENTS

| | | |
|---|---|---|
| EP | 1 123 898 A1 | 8/2001 |
| EP | 1 232 999 A1 | 8/2002 |
| JP | 61-077620 A1 | 4/1986 |
| JP | 06-127937 A1 | 5/1994 |

OTHER PUBLICATIONS

Tsuneji Sano et al., "Pervaporation Performance of Zeolite Membrane," Kagaku Kogyo, Feb. 1995, pp. 25-31.
U.S. Appl. No. 10/792,500, filed Mar. 3, 2004, Mori et al.

* cited by examiner

Primary Examiner—Rena Dye
Assistant Examiner—Lawrence Ferguson
(74) Attorney, Agent, or Firm—Burr & Brown

(57) ABSTRACT

A laminated zeolite composite is provided, including a MFI membrane constituted by a MFI type zeolite having a $SiO_2/Al_2O_3$ (molar ratio) of 40 to 100, and a porous substrate constituted by a MFI type zeolite having a $SiO_2/Al_2O_3$ (molar ratio) of 20 to 400, wherein the MFI membrane is formed on the porous substrate. The composite has high separation characteristics and high permeability.

6 Claims, 1 Drawing Sheet

US 7,252,876 B2

LAMINATED ZEOLITE COMPOSITE AND METHOD FOR PRODUCTION THEREOF

CROSS REFERENCE TO RELATED APPLICATIONS

This application is a continuation of International Application No. PCT/JP02/09317 having an international filing date of Sep. 12, 2002, which designated the United States, the entirety of which is incorporated herein by reference.

This application also claims the benefit of Japanese Application No. 2001-281675, filed Sep. 17, 2001, the entirety of which is incorporated herein by reference.

TECHNICAL FIELD

The present invention relates to a laminated zeolite composite and a method for producing the laminated zeolite composite.

BACKGROUND ART

Zeolite composite membranes obtained by forming a zeolite membrane on a substrate have been known and have been used as a gas separation membrane or a liquid separation membrane. With respect to such zeolite composite membranes, it is known that when the $SiO_2/Al_2O_3$ (molar ratio) of the membrane (hereinafter, it means a molar ratio when simply "$SiO_2/Al_2O_3$" is mentioned) varies, the interaction between the pore surface of zeolite and a molecule passing therethrough varies and the characteristic of the membrane when used as a separation membrane varies as well.

For example, p. 25 of an article by Yoji Sano and Yushi Kawakami in Kagaku Kogyo, February 1995 discloses a finding on the influence of $SiO_2/Al_2O_3$ on the permeation and separation characteristic of MFI type zeolite membrane (hereinafter referred to also as "MFI membrane") when water and alcohol are separated from each other by pervaporation using the membrane. It is known that the membrane shows striking alcohol selectivity when the $SiO_2/Al_2O_3$ thereof is increased.

As a specific example of the generally used MFI membrane, there can be mentioned a zeolite composite membrane obtained by forming a MFI membrane on an alumina substrate. With respect to such a zeolite composite membrane, it is known that, during the formation of the MFI membrane, aluminum in the alumina-made substrate dissolves into the MFI membrane and is taken into the skeleton of the MFI membrane and, as a result, the MFI membrane becomes a $SiO_2/Al_2O_3$— reduced MFI membrane (hereinafter this membrane is expressed also as "low-silica MFI membrane").

Also, JP-A-6-127937 discloses a self-supported MFI membrane not formed on any substrate (hereinafter this membrane is referred to as a "MFI self-supported membrane"), into which aluminum is taken and wherein the $SiO_2/Al_2O_3$ is reduced, and a method for the production thereof.

In the zeolite composite membrane obtained by forming a MFI membrane on an alumina substrate, however, it is impossible to strictly control the $SiO_2/Al_2O_3$ of the MFI membrane and, therefore, it is difficult to steadily synthesize a low-silica MFI membrane exhibiting uniform separation characteristic. Further, in synthesis of the MFI membrane, a structure-directing agent is added generally and it is necessary to remove the structure-directing agent by high-temperature calcination; however, since the substrate alumina and the MFI membrane (zeolite) differ in thermal expansion coefficient, the MFI membrane may generate cracks during calcination.

In the zeolite membrane described in JP-A-6-127937, since it is a MFI self-supported membrane, problems such as crack generation in MFI membrane due to difference in thermal expansion coefficient between substrate and zeolite can be avoided. Even in the method for the production of MFI membrane according to the above literature, however, it is described therein that the MFI membrane formed at the initial stage of synthesis has a large $SiO_2/Al_2O_3$ and the $SiO_2/Al_2O_3$ tends to become smaller with the growth of the membrane; therefore, a low-silica MFI membrane having small value in $SiO_2/Al_2O_3$ is obtainable only when the thickness of the membrane is made large. Consequently, the MFI membrane obtained exhibits permeation and separation characteristic as a low-silica MFI membrane, but has a large thickness and accordingly a small permeation factor and has a problem of low permeability.

The present invention has been made in view of such problems possessed by the prior art, and aims at providing a laminated zeolite composite having high separation characteristics and a high permeability, and a method for producing such a laminated zeolite composite.

SUMMARY OF THE INVENTION

According to the present invention, there is provided a laminated zeolite composite characterized in that it comprises a MFI membrane constituted by a MFI type zeolite having a $SiO_2/Al_2O_3$ (molar ratio) of 40 to 100, and a porous substrate constituted by a MFI type zeolite having a $SiO_2/Al_2O_3$ (molar ratio) of 20 to 400, wherein the MFI membrane is formed on the porous substrate.

In the present invention, the MFI membrane preferably has a thickness of 25 μm or less. Incidentally, the $SiO_2/Al_2O_3$ (molar ratio) of the MFI membrane may gradually decrease from the side of the membrane contacting the porous substrate toward the other side thereof.

The laminated zeolite composite of the present invention is suitably used for the separation of butane isomers or for the separation of propane and propylene.

According to the present invention, there is also provided a method for producing a laminated zeolite composite comprising the steps of immersing a porous substrate in a silica sol-containing sol for membrane formation, and forming a MFI membrane on the porous substrate under heating conditions; the method being characterized in that a porous substrate constituted by a MFI type zeolite having a $SiO_2/Al_2O_3$ (molar ratio) of 20 to 400 is immersed in a sol for membrane formation having a $SiO_2/Al_2O_3$ (molar ratio) in a range of 40 to 150 and a $Na_2O/Al_2O_3$ (molar ratio) of 15 or less.

In the present invention, it is preferred to form a MFI membrane constituted by a MFI type zeolite having a $SiO_2/Al_2O_3$ (molar ratio) of 40 to 100.

DETAILED DESCRIPTION OF THE INVENTION

Figure 1:
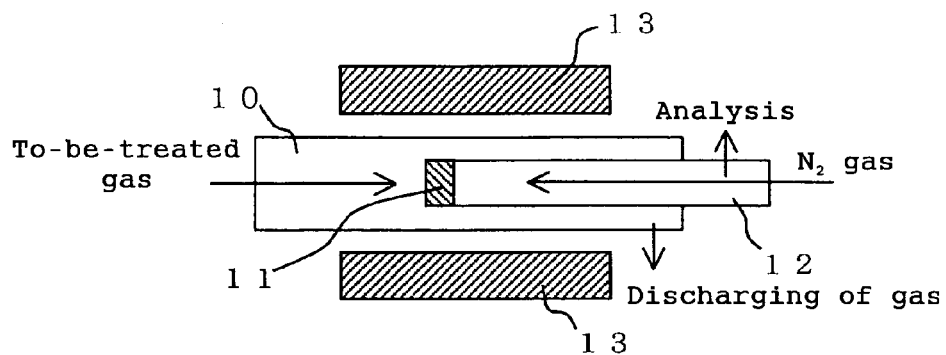
FIG. 1 is a schematic drawing showing a mode for carrying out the permeation and separation test of butane isomers.

Modes for carrying out the present invention are described below. However, the present invention is not restricted to the following modes and it should be construed that design change, improvement, etc. may be made appropriately based on the ordinary knowledge of those skilled in the art as long as there is no deviation from the gist of the present invention.

The first aspect of the present invention lies in a laminated zeolite composite characterized in that it comprises a MFI membrane constituted by a MFI type zeolite having a $SiO_2/Al_2O_3$ (molar ratio) of 40 to 100, and a porous substrate constituted by a MFI type zeolite having a $SiO_2/Al_2O_3$ (molar ratio) of 20 to 400, wherein the MFI membrane is formed on the porous substrate.

In the laminated zeolite composite of the present invention, the $SiO_2/Al_2O_3$ of the MFI membrane may gradually decrease from the side of the MFI membrane in contact with the porous substrate toward the other side of the MFI membrane. Incidentally, the term "gradually decrease" means that the $SiO_2/Al_2O_3$ decreases gradually within a range of 40 to 100. The details of the first aspect are described below.

The present invention has been completed based on a finding that there is a correlation between the $SiO_2/Al_2O_3$ of MFI membrane and the separation factor of butane isomers when the MFI membrane is used. That is, the laminated zeolite composite of the present invention obtained by forming a MFI membrane having a $SiO_2/Al_2O_3$ of 40 to 100, on a porous substrate composed of a MFI type zeolite and having a $SiO_2/Al_2O_3$ of 20 to 400, has a characteristic of gas separation, for example, separation of butane isomers.

In the above-mentioned article by Yoji Sano and Yushi Kawakami in Kagaku Kogyo, the influence of the $SiO_2/Al_2O_3$ of the MFI membrane on the permeation and separation characteristic of the MFI membrane in separation of water and alcohol, i.e. components separation when the to-be-treated material is a liquid is disclosed. It should be noted, however, that no mention is made therein of the influence on the gas separation characteristic when the to-be-treated material is a gas. The correlation between the $SiO_2/Al_2O_3$ of the MFI membrane and the characteristic of gas separation including separation of butane isomers has been found for the first time in the present invention.

Further, in the laminated zeolite composite of the present invention, since a MFI membrane is formed on a porous zeolite substrate, and since the membrane is composed of the same zeolite as the porous substrate, inconveniences such as crack generation in MFI membrane due to difference in thermal expansion coefficient between the porous substrate and the MFI membrane are avoided during production or use of the composite, and the MFI membrane keeps its function at a satisfactory level.

Incidentally, the term "$SiO_2/Al_2O_3$ (molar ratio)" referred to in the present invention represents a value obtained by a measurement using energy dispersive spectroscopy (EDS).

A MFI membrane having a $SiO_2/Al_2O_3$ less than 40 is not preferred because the MFI membrane tends to generate cracks on the surface. Meanwhile, a MFI membrane having a $SiO_2/Al_2O_3$ greater than 100 is not preferred because, when used as a separation membrane the MFI membrane hardly exhibits any unique gas separation characteristics. The $SiO_2/Al_2O_3$ of the MFI membrane is preferably 45 to 90, more preferably 50 to 80 from the standpoint of providing superior performance as a separation membrane. In order to allow the MFI membrane to have a $SiO_2/Al_2O_3$ of 40 to 100, the $SiO_2/Al_2O_3$ of the porous substrate is preferably 20 to 400. The $SiO_2/Al_2O_3$ of the porous substrate is more preferably 40 to 100, which is the same as that in the MFI membrane.

In the laminated zeolite composite of the present invention, the MFI membrane preferably has a thickness of 25 μm or less, whereby the MFI membrane has high separation characteristic and excellent permeability. In order for the MFI membrane to exhibit particularly excellent permeability, the thickness of the MFI membrane is preferably 17 μm or less, more preferably 13 μm or less. In the present invention, there is no restriction as to the lower limit of the thickness of the MFI membrane. It should be noted, however, that the lower limit is sufficient at 0.1 μm or more in view of the function the MFI membrane when used as a separation membrane and the practical producibility of the MFI membrane, for example.

Examples of the shape of the laminated zeolite composite of the present invention include a bar shape, a pellet shape, a flat sheet shape, a tube shape, a monolithic shape and a honeycomb shape.

By utilizing the advantages of having an excellent separation characteristic and permeability and the property of hardly generating cracks, etc., the laminated zeolite composite of the present invention can be suitably used as a separation membrane for carrying out the separation of butane isomers or the separation of propane and propylene.

Next, description is made of the second aspect of the present invention, which is a method for producing a laminated zeolite composite comprising the steps of immersing a porous substrate in a silica sol-containing sol for membrane formation, and forming a MFI membrane on the porous substrate under heating conditions. The method is characterized in that a porous substrate constituted by a MFI type zeolite having a $SiO_2/Al_2O_3$ (molar ratio) of 20 to 400 is immersed in a sol for membrane formation having a $SiO_2/Al_2O_3$ (molar ratio) of 40 to 150 and a $Na_2O/Al_2O_3$ (molar ratio) of 15 or less. In the present invention, it is preferred that a MFI membrane constituted by a MFI type zeolite and having a $SiO_2/Al_2O_3$ of 40 to 100 is formed. The details of the second aspect are described below. Incidentally, the term "$Na_2O/Al_2O_3$" mentioned hereinafter refers to a molar ratio.

When a sol is used for membrane formation having a $SiO_2/Al_2O_3$ of less than 40 or more than 150, the obtained MFI membrane is unable to have a $SiO_2/Al_2O_3$ of 40 to 100. Even when a sol is used for membrane formation having a $SiO_2/Al_2O_3$ of 40 to 150, but when the sol has a $Na_2O/Al_2O_3$ of greater than 15, a MFI membrane is formed having a $SiO_2/Al_2O_3$ of less than 40, which is not preferred.

In order for the MFI membrane formed to reliably have a $SiO_2/Al_2O_3$ of 40 to 100, it is preferred to use a sol for membrane formation having a $SiO_2/Al_2O_3$ of 50 to 130, and it is more preferred to use a $SiO_2/Al_2O_3$ of 55 to 120. It is also preferred to use a sol for membrane formation having a $Na_2O/Al_2O_3$ of 13 or less, and it is more preferred to use a sol for membrane formation having a $Na_2O/Al_2O_3$ of 10 or less. Incidentally, there is no particular restriction as to the lower limit of the $Na_2O/Al_2O_3$ of the sol for membrane formation used in the present invention. It should be noted, however, that the lower limit may be 1 or more in view of, for example, the practical production conditions of laminated zeolite composite.

In the present invention, a porous substrate having a $SiO_2/Al_2O_3$ of 20 to 400 is immersed in the sol for membrane formation. As the method for producing such a porous substrate, a known conventional method may be used. In an example, tetrapropylammonium hydroxide (TPAOH), a silica sol, NaAlO$_2$, etc. are mixed at desired SiO$_2$/Al$_2$O$_3$ and TPAOH/SiO$_2$ (molar ratio). The resulting mixture is stirred and kneaded with heating, to vaporize water to obtain a dry gel, and the dry gel is ground to obtain a powder. The powder is formed, by an appropriate forming method to obtain a formed article and then the formed article is subjected to, for example, a reaction under a steam pressure, whereby a porous substrate having a SiO$_2$/Al$_2$O$_3$ in the desired range can be produced. Incidentally, as the appropriate forming method, an ordinary ceramic forming method such as extrusion forming, CIP forming, slip casting or the like may be used.

In the above example of the method of producing the porous substrate, it is preferred to use NaAlO$_2$ as a Na and Al source. When the Na$_2$O/Al$_2$O$_3$ is larger than 1, the porous substrate obtained has crystalline Na separated thereon; when the Na$_2$O/Al$_2$O$_3$ is smaller than 1, the obtained porous substrate has a low strength. NaAlO$_2$ is preferred because it contains Na and Al in a 1:1 (molar ratio) and the Na$_2$O/Al$_2$O$_3$ can be controlled strictly at 1.

The porous substrate produced by the above method, for example, is immersed in the sol for membrane formation having a SiO$_2$/Al$_2$O$_3$ of 40 to 150 and a Na$_2$O/Al$_2$O$_3$ of 15 or less. A reaction is allowed to take place under a heating condition, and a MFI membrane is thereby formed on the porous substrate. Here, the term "under a heating condition" refers to a reaction in a temperature range of 100 to 200° C. in a pressure vessel.

The obtained membrane-formed substrate is appropriately heated to at about 500 to 600° C. in, for example, an electric oven and held for about 4 to 10 hours at this temperature to remove the structure-directing agent (TPA) used. The holding time and the heating and cooling rate are appropriately determined so as to match the sizes of membrane-formed substrate and electric oven. Incidentally, in the present invention, the thickness of the MFI membrane formed is preferably set at 25 μm or less, more preferably at 17 μm or less, particularly preferably at 13 μm or less. Thereby, a laminated zeolite composite having high permeability can be obtained.

Incidentally, the thickness of the MFI membrane can be controlled, for example, by controlling the reaction time.

In the present invention, there is no restriction as to the lower limit of the thickness of the MFI membrane formed. However, the lower limit is sufficient at 0.1 μm or more in view of, for example, the function of MFI membrane as a separation membrane and the practical producibility of the MFI membrane.

In the present invention, it is preferred to form a MFI membrane having a SiO$_2$/Al$_2$O$_3$ ratio of 40 to 100 because the MFI membrane can allow the resulting laminated zeolite composite to have a particularly excellent function as a separation membrane. In order for the MFI membrane to exhibit a particularly excellent function as a separation membrane, it is more preferred for the MFI membrane to have a SiO$_2$/Al$_2$O$_3$ ratio of 45 to 90, and it is particularly preferred to have a SiO$_2$/Al$_2$O$_3$ ratio of 50 to 80.

EXAMPLES

The present invention is specifically described below by way of Examples. However, the present invention is not restricted to these Examples.

Examples 1 and 2 and Comparative Examples 1-6

1. Method of Producing Substrate A

To 16.27 g of a 10% aqueous TPAOH solution (a product of Wako Pure Chemical Industries, Ltd.) were added 0.656 g of NaAlO$_2$ (a product of Wako Pure Chemical Industries, Ltd.) and 40.05 g of about 30 wt % silica sol (Snowtex S, a product of Nissan Chemical Industries, Ltd.). The mixture was stirred at room temperature for 1 hour using a desk shaker and then stirred and kneaded with heating at about 80° C. using a hot stirrer, to vaporize water, whereby a colorless dry gel was obtained.

The dry gel was ground to obtain a powder, after which the powder was subjected to uniaxial pressing with a die at a total pressure of 2 ton to obtain a formed article having a disc shape having a diameter of 19 mm and a thickness of 2 mm. The formed article was set on a fluororesin plate in a stainless steel pressure vessel with a fluororesin inner cylindrical container placing distilled water of the same weight as the formed article, in a state that there is no contact between the formed article and the water. After the pressure vessel was placed in an oven of 180° C., the contents of the vessel were subjected to a reaction under a self steam pressure for 12 hours, whereby a porous substrate (porous substrate A) was obtained.

The crystal phase of the obtained porous substrate A was examined by X-ray diffractometry. As a result, porous substrate A was found to be an MFI type zeolite of perfect crystal. Incidentally, the crystal phase of zeolite when the X-ray diffractiometry showed only a broad halo and no clear peak in a region of 20 to 300 (CuKα), was expressed as "amorphous"; when a zeolite peak was seen even slightly, the crystal phase was expressed as "under crystallization"; and when all sharp peaks of zeolite were seen clearly and there was no halo, the crystal phase was expressed as a "perfect crystal." Incidentally, the SiO$_2$/Al$_2$O$_3$ of the porous substrate A was 50.

2. Method of Producing Porous Substrate B

To 16.27 g of a 10% aqueous TPAOH solution (a product of Wako Pure Chemical Industries, Ltd.) was added 40.05 g of about 30 wt % silica sol (Snowtex S, a product of Nissan Chemical Industries, Ltd.). The mixture was stirred at room temperature for 1 hour using a desk shaker and then stirred and kneaded with heating at about 80° C. using a hot stirrer, to vaporize water, whereby a colorless dry gel was obtained. The later operation was conducted in the same manner as in production of the porous substrate A, to obtain a porous substrate (porous substrate B).

The crystal phase of the obtained porous substrate B was examined by X-ray diffractometry. As a result, porous substrate B was found to be an MFI type zeolite of perfect crystal. Incidentally, the SiO$_2$/Al$_2$O$_3$ of the porous substrate B was 500 or more.

3. Formation of MFI Membranes

There were mixed, so as to give compositions shown in Table 1, various raw materials, i.e. a 10% aqueous TPAOH solution (a product of Wako Pure Chemical Industries, Ltd.), distilled water, tetrapropylammonium bromide (a product of Wako Pure Chemical Industries, Ltd.), aluminum sulfate (14 to 18 hydrates) (a product of Wako Pure Chemical Industries, Ltd.), a 30 wt % silica sol (Snowtex S, a product of Nissan Chemical Industries, Ltd.) and a 4N aqueous sodium hydroxide solution (a product of Wako Pure Chemical Industries, Ltd.). The mixture was stirred at room temperature for 60 minutes using a desk shaker to produce a sol for membrane formation. The sol for membrane formation was placed in a 100 ml-stainless steel-made pressure vessel with a fluororesin-made inner cylindrical container. Therein was immersed one of the above-produced porous substrates A or B. After the pressure vessel was placed in an oven of 180° C., the contents of the vessel were subjected to a reaction for 8 hours, whereby a MFI membrane was formed on the porous substrate. The resulting membrane-formed substrate was placed in an electric oven, the substrate temperature was elevated to 550° C. and then held at this temperature for 4 hours to remove the TPA, whereby the laminated zeolite composites of Examples 1 to 2 and Comparative Examples 1 to 6 were produced.

Incidentally, the $SiO_2/Al_2O_3$ and $Na_2O/Al_2O_3$ of each sol for membrane formation and the $SiO_2/Al_2O_3$ of each porous substrate are shown in Table 2.

scanning the whole surface of the cross section of the MFI membrane. The results thereof are shown in Table 3.

3. Permeation and Separation Test

A permeation and separation test for butane isomers was carried out by the Wicke-Kallenbach method. FIG. 1 schematically shows a mode for carrying out the permeation and separation test for butane isomers. FIG. 1 shows a state in which there is placed, inside a permeation and separation test apparatus 10, a separated gas-holding unit 12 fitted with a laminated zeolite composite 11. Incidentally, the permeation and separation test apparatus 10 is heatable by an electric oven 13.

A mixed gas containing about 5% by volume of isobutane and about 5% by volume of normal butane (n-butane) was fed to one side of the laminated zeolite composite 11 using

TABLE 1

| | 10% tetrapropylammonium hydroxide solution (g) | Distilled water (g) | Tetrapropyl-ammoniumbromide (g) | Aluminum sulfate (g) | 30 wt % silica sol (g) | 4N aqueous sodium-hydroxide solution (g) | Porous substrate |
|---|---|---|---|---|---|---|---|
| Exam. 1 | 15.26 | 49.85 | 0 | 0.21 | 6 | 1 | A |
| Exam. 2 | 15.26 | 49.85 | 0 | 0.21 | 6 | 2 | A |
| Comp. Exam. 1 | 15.26 | 49.85 | 1.995 | 0 | 6 | 0 | B |
| Comp. Exam. 2 | 15.26 | 49.85 | 0 | 0.21 | 6 | 1 | B |
| Comp. Exam. 3 | 15.26 | 49.85 | 0 | 0.21 | 6 | 3 | B |
| Comp. Exam. 4 | 10.17 | 49.85 | 1.995 | 0.21 | 6 | 1.6 | B |
| Comp. Exam. 5 | 15.26 | 49.85 | 1.995 | 0 | 6 | 0 | A |
| Comp. Exam. 6 | 15.26 | 49.85 | 0 | 0.21 | 6 | 3 | A |

TABLE 2

| | Sol for membrane formation | | $SiO_2/Al_2O_3$ (molar ratio) of porous substrate |
|---|---|---|---|
| | $SiO_2/Al_2O_3$ (molar ratio) | $Na_2O/Al_2O_3$ (molar ratio) | |
| Exam. 1 | 40 to 150 | <15 | 50 |
| Exam. 2 | 40 to 150 | <15 | 50 |
| Comp. Exam. 1 | >150 | — | >500 |
| Comp. Exam. 2 | 40 to 150 | <15 | >500 |
| Comp. Exam. 3 | 40 to 150 | >15 | >500 |
| Comp. Exam. 4 | 40 to 150 | <15 | >500 |
| Comp. Exam. 5 | >150 | — | 50 |
| Comp. Exam. 6 | 40 to 150 | >15 | 50 |

Evaluation of MFI membranes (separation membranes)

1. Thickness Measurement and Surface Observation of Each MFI Membrane

By observing the cross-section and surface of each MFI membrane using a SEM, the thickness of each MFI membrane was measured and the crack generation at the surface of each MFI membrane was examined. When cracks were confirmed by the SEM observation, the sample was rated as "present," and when no cracks were confirmed, the sample was rated as "not present."

The thickness of each MFI membrane formed on each laminated zeolite composite was 15 to 25 μm. The result of examination of the generation of cracks at the surface of each MFI membrane is shown in Table 3.

2. Determination of $SiO_2/Al_2O_3$

The $SiO_2/Al_2O_3$ ratio of MFI membrane was determined by EDS. The determination of the $SiO_2/Al_2O_3$ ratio of the MFI membrane according to EDS was carried out by a $N_2$ gas as a carrier gas, under a heating condition of 200° C., and the gas after permeation, at the opposite side of the laminated zeolite composite was swept by a $N_2$ gas and analyzed by gas chromatography. The separation factor of butane isomers is shown in Table 3. Incidentally, the separation factor of butane isomers is a value determined by the following expression, wherein $X_n$ and $X_{iso}$ are, respectively, the molar concentrations of n-butane and isobutane at the supply side of the gas, and $Y_n$ and $Y_{iso}$ are, respectively, the molar concentrations of n-butane and isobutane at the permeation side of the permeated gas:

Separation factor of butane isomers=$(Y_n/Y_{iso})/(X_n/X_{iso})$.

TABLE 3

| | Crack generation at surface of MFI membrane | $SiO_2/Al_2O_3$ (molar ratio) of MFI membrane | Separation factor of butane isomers |
|---|---|---|---|
| Exam. 1 | Not present | 52 | 84.3 |
| Exam. 2 | Not present | 79 | 62.0 |
| Comp. Exam. 1 | Not present | 225 | 16.0 |
| Comp. Exam. 2 | Not present | 130 | 16.3 |
| Comp. Exam. 3 | Present | 26 | 19.8 |
| Comp. Exam. 4 | Not present | 107 | 14.2 |
| Comp. Exam. 5 | Not present | 201 | 11.7 |
| Comp. Exam. 6 | Present | 29 | 14.2 |

Figure 2:
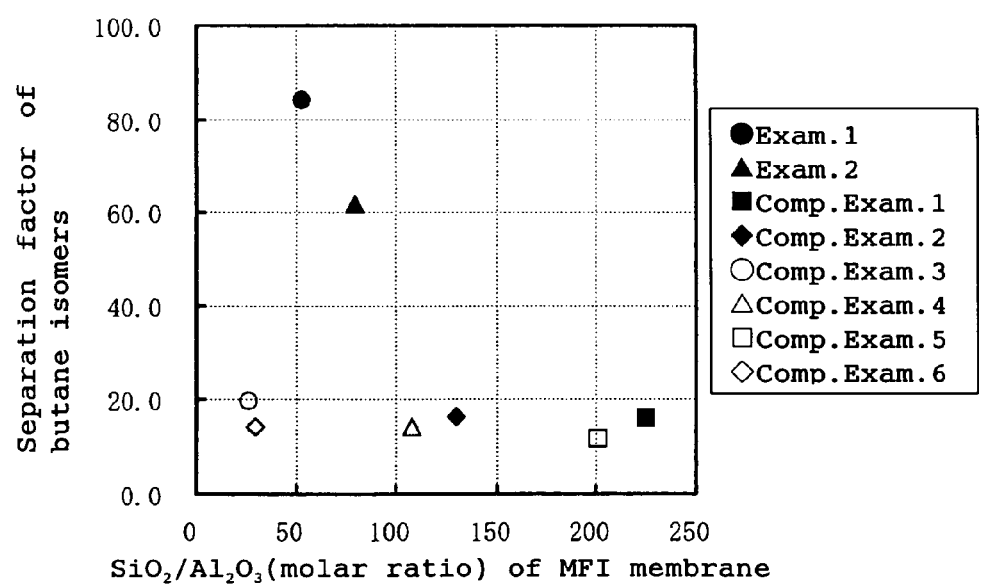
FIG. 2 is a graph wherein the separation factor of butane isomers is plotted against the $SiO_2/Al_2O_3$ of MFI membrane.

FIG. 2 is a graph showing the separation factor butane isomers are plotted against the $SiO_2/Al_2O_3$ value of each MFI membrane.

Discussion

In order to produce a laminated zeolite composite exhibiting excellent separation characteristics, it is required that (1) the porous substrate used has a $SiO_2/Al_2O_3$ of 20 to 400, (2) the sol used for the membrane formation has a $SiO_2$/

$Al_2O_3$ of 40 to 150, and (3) the sol used for the membrane formation has a $Na_2O/Al_2O_3$ of 15 or less. Explanation is made below on each Example and each Comparative Example, based on the results obtained above.

In Example 1, the porous substrate had a $SiO_2/Al_2O_3$ of 50 and the sol used for the membrane formation had a $SiO_2/Al_2O_3$ of 95 and a $Na_2O/Al_2O_3$ of 6.3, and all of the above requirements (1) to (3) for producing a laminated zeolite composite exhibiting excellent separation characteristic were satisfied. In Example 2, the porous substrate had a $SiO_2/Al_2O_3$ of 50 and the sol used for the membrane formation had a $SiO_2/Al_2O_3$ of 95 and a $Na_2O/Al_2O_3$ of 12.6, and all of the above requirements (1) to (3) for producing a laminated zeolite composite exhibiting excellent separation characteristic were satisfied.

Meanwhile, in Comparative Examples 1 to 4, porous substrate B having a $SiO_2/Al_2O_3$ of >400 was used and requirement (1) was not satisfied. Further, in Comparative Example 1, the sol used for the membrane formation had a $SiO_2/Al_2O_3$ of >150 and requirement (2) was not satisfied. In Comparative Example 3, the sol used for the membrane formation had a $Na_2O/Al_2O_3$ of 18.9 and requirement (3) was not satisfied.

In Comparative Examples 5 and 6, porous substrate A having a $SiO_2/Al_2O_3$ of 50 was used and requirement (1) was satisfied. However, in Comparative Example 5, the sol used for the membrane formation had a $SiO_2/Al_2O_3$ of >150 and requirement (2) was not satisfied. In Comparative Example 6, the sol used for the membrane formation had a $Na_2O/Al_2O_3$ of 18.9 and requirement (3) was not satisfied.

It is clear from the results of Table 3 and FIG. 2 that Examples 1 and 2, compared with Comparative Examples 1 to 6, each show a very high separation factor for n-butane and isobutane. That is, it is clear that the laminated zeolite composites of Examples 1 and 2, as compared with those of Comparative Examples 1 to 6, each have excellent separation characteristics and hardly generate inconveniences such as cracks on the MFI membranes.

Incidentally, the laminated zeolite composites of Examples 1 and 2, as compared with those of Comparative Examples 1 to 6, showed a high separation factor of about 1.5 times, also in separation of propane and propylene.

INDUSTRIAL APPLICABILITY

As described above, in the laminated zeolite composite of the present invention, the MFI membrane and the porous substrate each have a $SiO_2/Al_2O_3$ in a given range and the MFI membrane is formed at a given thickness on such a porous substrate. Therefore, the present laminated zeolite composite has high separation characteristics and high permeability and can be suitably used, for example, in the separation of butane isomers or of propane and propylene.

According to the present method for producing a laminated zeolite composite, since a porous substrate having a $SiO_2/Al_2O_3$ in a given range is immersed in a sol used for the membrane formation having a $SiO_2/Al_2O_3$ in a given range, the MFI membrane formed can easily have a $SiO_2/Al_2O_3$ in a predetermined range.

The invention claimed is:

1. A laminated zeolite composite consisting of:
   a MFI membrane comprising a MFI type zeolite and having a $SiO_2/Al_2O_3$ (molar ratio) of 40 to 100; and
   a porous substrate comprising a MFI type zeolite and having a $SiO_2/Al_2O_3$ (molar ratio) of 20 to 400;
   wherein the MFI membrane is formed on the porous substrate.

2. The laminated zeolite composite according to claim 1, wherein the MFI membrane has a thickness of 25 µm or less.

3. The laminated zeolite composite according to claim 1, wherein the $SiO_2/Al_2O_3$ (molar ratio) of the MFI membrane decreases gradually from a side of the membrane contacting the porous substrate toward other side thereof.

4. The laminated zeolite composite according to claim 1, which is used for separation of butane isomers.

5. The laminated zeolite composite according to claim 1, which is used for separation of propane and propylene.

6. The laminated zeolite composite according to claim 2, wherein the $SiO_2/Al_2O_3$ (molar ratio) of the MFI membrane decreases gradually from a side of the membrane contacting the porous substrate toward other side thereof.

* * * * *